United States Patent
Gardeski et al.

(10) Patent No.: US 9,788,981 B2
(45) Date of Patent: Oct. 17, 2017

(54) SYSTEMS FOR DEPLOYING MEDICAL DIAGNOSTICS AND/OR THERAPY AND DELIVERY TOOLS THEREOF

(71) Applicant: Medtronic, Inc., Minneapolis, MN (US)

(72) Inventors: Kenneth C. Gardeski, Plymouth, MN (US); Nathan A. Grenz, Shoreview, MN (US); Xiaonan Shen, Shoreview, MN (US); Michael R. Leners, St. Francis, MN (US); Lonnie D. Ronning, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 65 days.

(21) Appl. No.: 14/548,323

(22) Filed: Nov. 20, 2014

(65) Prior Publication Data
US 2016/0143758 A1    May 26, 2016

(51) Int. Cl.
*A61N 1/05*    (2006.01)
*A61F 2/95*    (2013.01)

(52) U.S. Cl.
CPC ............... *A61F 2/95* (2013.01); *A61N 1/056* (2013.01); *A61N 1/057* (2013.01); *A61N 2001/0585* (2013.01)

(58) Field of Classification Search
None
See application file for complete search history.

(56) References Cited

U.S. PATENT DOCUMENTS

| 4,519,403 A | 5/1985 | Dickhudt |
| 5,443,492 A | 8/1995 | Stokes et al. |
| 5,766,234 A * | 6/1998 | Chen ................. A61B 17/00234 600/373 |
| 5,991,668 A | 11/1999 | Leinders et al. |
| 6,039,727 A * | 3/2000 | Javier, Jr. ................ A61B 18/22 606/10 |
| 6,159,198 A * | 12/2000 | Gardeski ........... A61M 25/0668 604/161 |

(Continued)

OTHER PUBLICATIONS

(PCT/US2015/061072) PCT Notification of Transmittal of the International Search Report and the Written Opinion of the International Searching Authority, dated Feb. 3, 2016, 10 pages.

*Primary Examiner* — Lynsey Eiseman
*Assistant Examiner* — Qingjun Kong (57) ABSTRACT

A delivery tool of a system for deploying medical diagnostics and/or therapy includes a deployment member and a sheath. An elastic cantilever element secured to a tubular sidewall of the deployment member, in proximity to a distal opening of a lumen formed by the sidewall, is spring biased to extend outward from the sidewall. When the cantilever element is received within the sheath, a sheath sidewall pushes the cantilever element inward, against the spring bias thereof, and a radius of curvature of the cantilever element approximately conforms to that of an outer surface of the deployment member sidewall. A helical track for receiving passage of a medical device helix fixation element therein may extend around a perimeter of the deployment member lumen, wherein a distal terminal end of the track is located in close proximity to the distal opening and generally opposite a free end of the cantilever element.

19 Claims, 9 Drawing Sheets

(56) References Cited

U.S. PATENT DOCUMENTS

| | | | |
|---|---|---|---|
| 6,408,214 B1* | 6/2002 | Williams | A61M 25/0041 |
| | | | 607/122 |
| 7,251,532 B2 | 7/2007 | Hess et al. | |
| 7,529,584 B2 | 5/2009 | Laske et al. | |
| 7,801,624 B1 | 9/2010 | Flannery et al. | |
| 7,860,580 B2 | 12/2010 | Falk et al. | |
| 8,219,213 B2 | 7/2012 | Sommer et al. | |
| 2003/0023296 A1 | 1/2003 | Osypka | |
| 2005/0004560 A1* | 1/2005 | Cox | A61L 29/085 |
| | | | 606/1 |
| 2005/0065589 A1 | 3/2005 | Schneider et al. | |
| 2006/0264905 A1* | 11/2006 | Eskridge | A61M 25/0021 |
| | | | 604/523 |
| 2008/0183257 A1* | 7/2008 | Imran | A61N 1/0558 |
| | | | 607/117 |
| 2013/0325094 A1 | 12/2013 | Sommer et al. | |
| 2014/0276696 A1* | 9/2014 | Schneider | A61B 17/320758 |
| | | | 606/15 |

\* cited by examiner

SYSTEMS FOR DEPLOYING MEDICAL DIAGNOSTICS AND/OR THERAPY AND DELIVERY TOOLS THEREOF

TECHNICAL FIELD

The present disclosure is related to medical diagnostics and/or therapy, and more particularly to systems and tools for the deployment thereof.

BACKGROUND

Figure 1A:
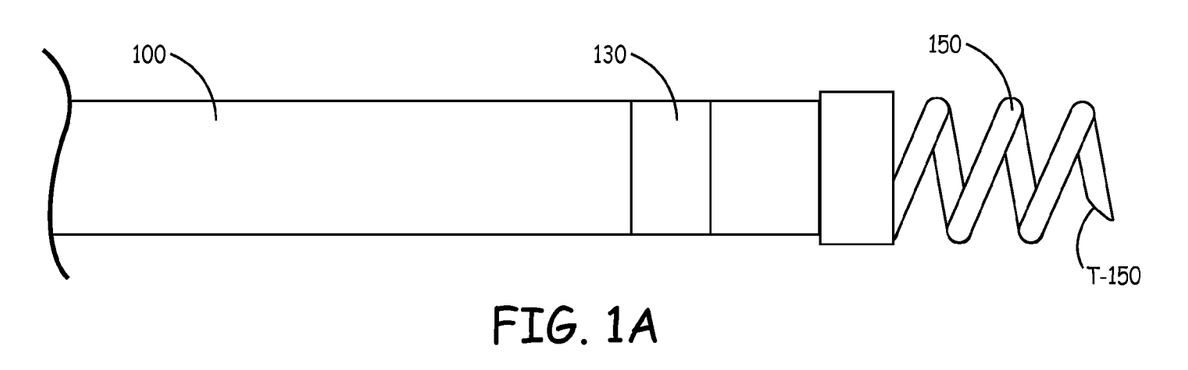
FIGS. 1A-B are plan views of portions of exemplary implantable medical devices.
Figure 1B:
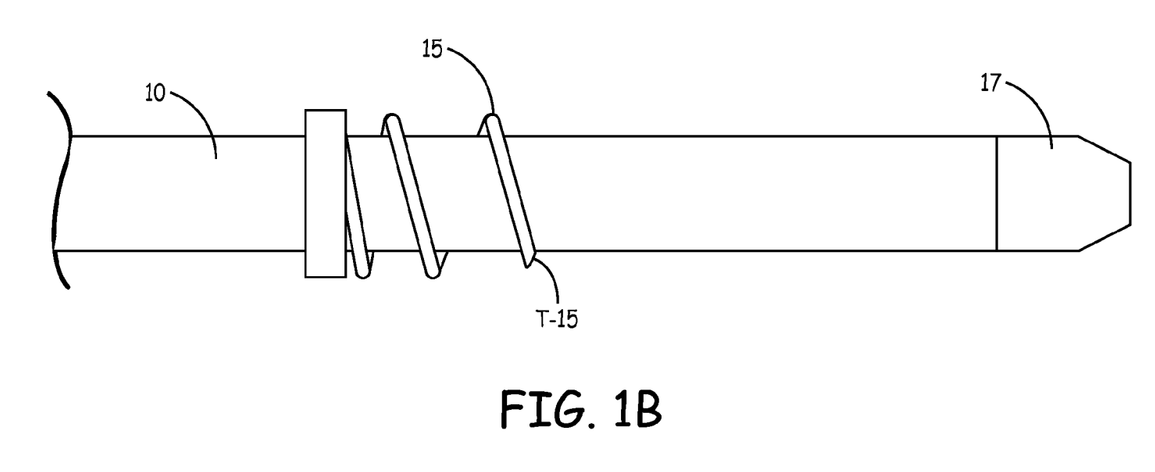
Figure 2:
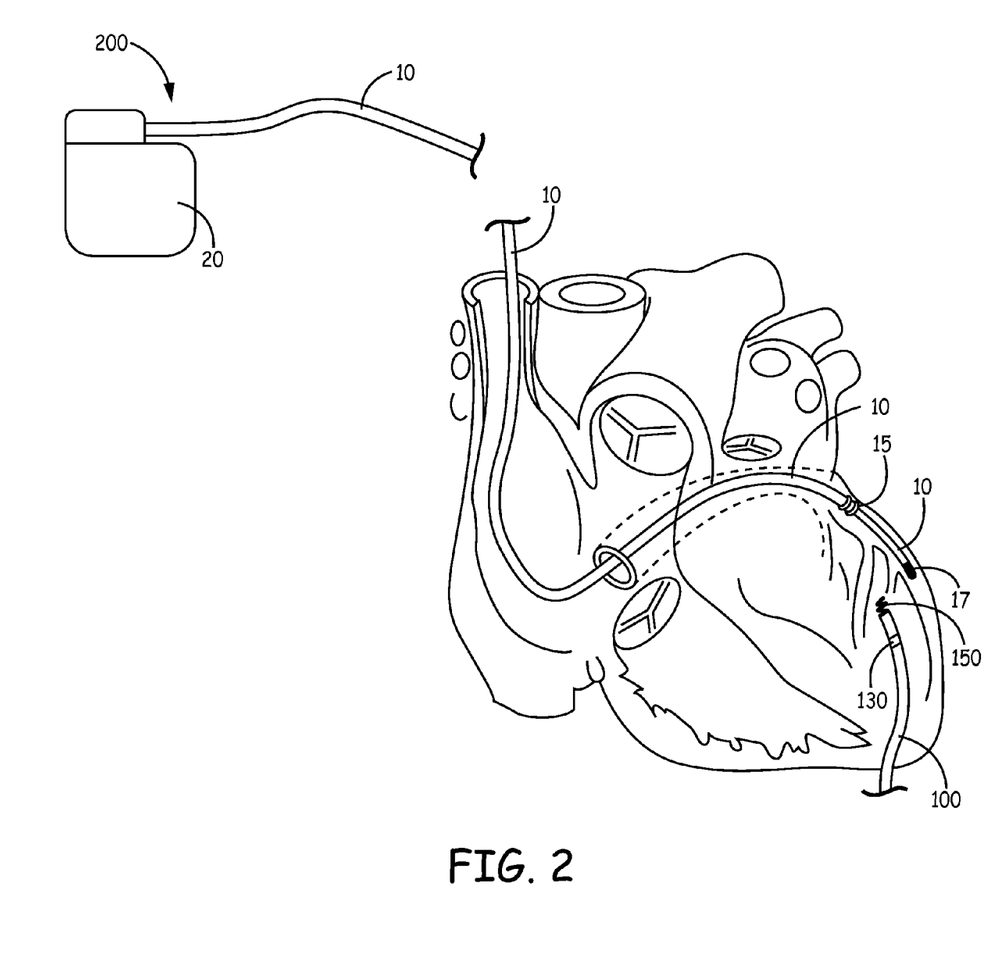
FIG. 2 is a schematic depicting potential implant sites for the devices of FIGS. 1A-B.

Implantable medical devices providing diagnostics and/or therapy delivery are often fixed to an implant site within a body of a patient by a helical element. FIGS. 1A-B are plan views of portions of exemplary medical devices, each of which include such an element for fixation; and FIG. 2 is a schematic depicting potential implant sites for the devices. FIGS. 1A and 2 illustrate a first of the exemplary medical devices including an elongate body 100 and a helix fixation element 150 coupled thereto and terminating a distal end thereof. FIGS. 1A-2 further illustrate an electrode 130 mounted around body 100 and offset proximally from helix fixation element 150. FIGS. 1B and 2 illustrate a second exemplary medical device 200 including an elongate body 10 to which a helix fixation element 15 is coupled such that element 15 extends around body 10. FIGS. 1B and 2 further illustrate an electrode 17 terminating a distal end of body 10, being offset distally from helix fixation element 15. With reference to FIGS. 1A-B, each helix fixation element 150, 15 includes a piercing tip T-150, T-15 for engaging tissue at the implant site. FIG. 2 shows device 200 also including a pulse generator 20, such as is known to those skilled in the art, which is located in a pectoral region of the patient, and to which elongate body 10 is coupled. Although not shown, body 100 may be coupled to a similar pulse generator which is located in another region of the patient, for example, abdominal. Either of helix fixation elements 150, 15 may also function as an electrode, for example, for bipolar pacing and sensing in conjunction with the corresponding electrode 130, 17. Alternately, each medical device need not include the corresponding electrode 130, 17, and helix fixation element 150, 15 may or may not function as an electrode.

Figure 3A:
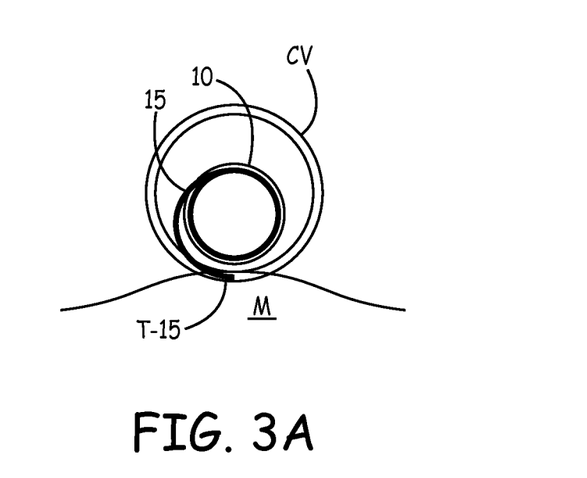
FIGS. 3A-B are cross-section schematics of the exemplary devices of FIGS. 1A-B implanted at each site of FIG. 2.
Figure 3B:
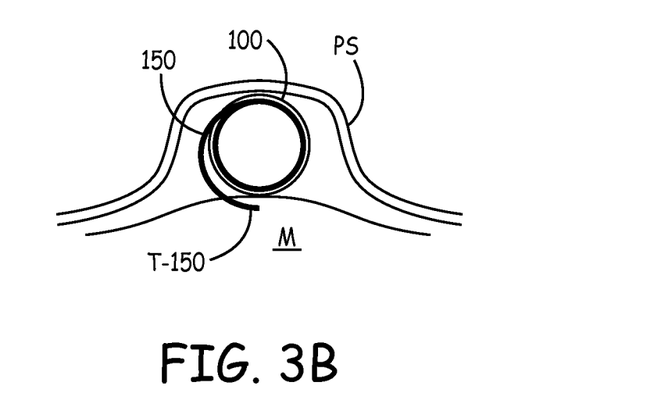

With further reference to FIG. 2, elongate body 10 is implanted trans-venous, at an epicardial site within a cardiac vein CV, and elongate body 100 is implanted trans-thoracic, also at an epicardial site, but outside any of the cardiac blood vessels. FIGS. 3A-B are cross-section schematics of the exemplary devices of FIGS. 1A-B implanted at each site. FIG. 3A illustrates body 10 located within cardiac vein CV, and piercing tip T-15 of helix fixation element 15 engaging tissue of the myocardium M. FIG. 3B illustrates body 100 located between the myocardium M and pericardial sac PS, and piercing tip T-150 engaging tissue of the myocardium M. In each exemplary case, initial engagement of fixation element 15, 150 with myocardium M, as opposed to within an opposing wall of cardiac vein CV or pericardial sac PS, is preferred for more stable fixation. Furthermore, if helix fixation element 15, 150 also functions as an electrode for cardiac pacing, engagement thereof with the myocardium M may be important for adequate pacing thresholds. Those skilled in the art appreciate the difficulties deploying body 10, 100 with piercing tip T-15, T-150 oriented for the illustrated engagement, thus various systems including delivery tools that are directed toward facilitating such a deployment are known in the art. Yet there is still a need for new systems and delivery tools thereof that facilitate deployment of medical diagnostics and/or therapy with helix fixation members of implantable medical devices oriented for the preferred initial engagement piercing tips thereof with tissue at desired implant sites.

SUMMARY

According to embodiments of the present invention, a delivery tool of a system for deploying medical diagnostics and/or therapy includes a deployment member and a sheath that receives passage of the deployment member therethrough, wherein the deployment member includes a tubular sidewall forming an elongate lumen that receives passage of an elongate body of a medical device of the system therethrough. The deployment member of the delivery tool further includes an elastic cantilever element, which is secured to the tubular sidewall in proximity to a distal opening of the deployment member lumen, wherein the cantilever element is spring biased to extend outward from the sidewall, in a direction approximately orthogonal to a longitudinal axis of the tool. But, when the cantilever element is received within a lumen of the sheath, formed by a sidewall thereof, the sheath sidewall pushes the cantilever element inward, toward the longitudinal axis, against the spring bias thereof, and a radius of curvature of the cantilever element approximately conforms to a curvature of an outer surface of the deployment member sidewall. A distal-most edge that defines the distal opening of the sheath lumen may extend in a plane that forms an acute angle with respect to the longitudinal axis of the tool.

The elongate body of the medical device has a helix fixation element coupled thereto, and, in some embodiments, the deployment member further includes a helical track configured to receive passage of the helix fixation element therein, wherein the helical track extends around a perimeter of the deployment member lumen within a distal segment of the deployment member that is terminated by a distal-most edge of the deployment member sidewall. A distal terminal end of the helical track is located in close proximity to the distal-most edge, and is generally opposite a free end of the cantilever element, when the cantilever element extends outward from the deployment member sidewall according the spring bias thereof. According to some embodiments, the distal-most edge of the deployment member sidewall includes a first section and a second section, wherein the first section is recessed from the second section along the longitudinal axis of the tool, and the distal terminal end of the helical track lies within a longitudinal gap between the first section and the second section.

BRIEF DESCRIPTION OF THE DRAWINGS

The following drawings are illustrative of particular embodiments and do not limit the scope of the disclosure. The drawings are not to scale (unless so stated) and are intended for use in conjunction with the explanations in the following detailed description. Embodiments will hereinafter be described in conjunction with the appended drawings wherein like numerals/letters denote like elements, and.

DETAILED DESCRIPTION

The following detailed description is exemplary in nature and is not intended to limit the scope, applicability, or configuration of inventive embodiments disclosed herein in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figure 4A:
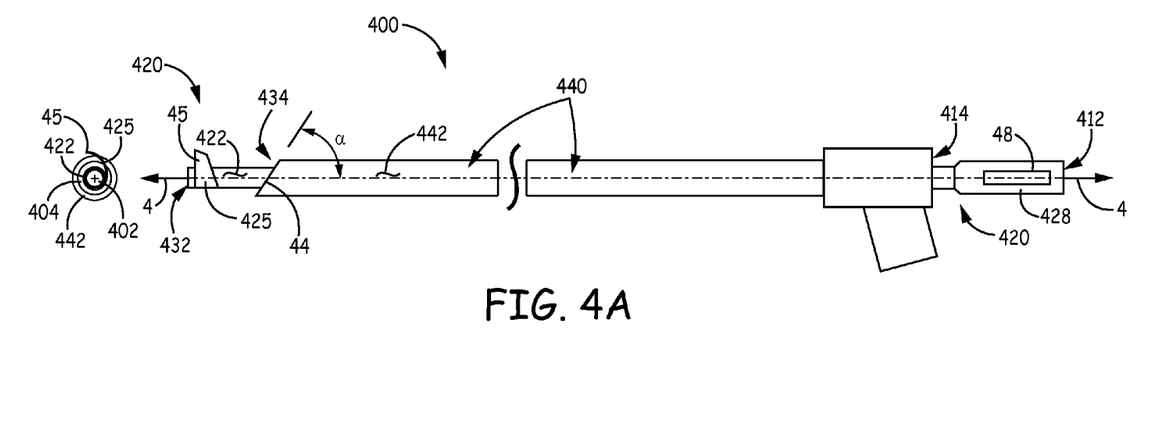
FIG. 4A is a plan view and corresponding end view of a delivery tool that may be included, for example, with one of the exemplary devices of FIGS. 1A-B, in a system for deployment of medical diagnostics and/or therapy, according to some embodiments.

FIG. 4A is a plan view and corresponding end view of a delivery tool 400 that may be included, for example, with one of the exemplary devices of FIGS. 1A-B, in a system for deployment of medical diagnostics and/or therapy, according to some embodiments. FIG. 4A illustrates tool 400 including a deployment member 420 and a sheath 440, wherein each includes a tubular sidewall 422, 442, and wherein an elongate lumen 404 formed by sheath sidewall 442 receives passage of deployment member 420 therethrough. Tubular sidewall 422 of deployment member 420 also forms an elongate lumen 402, which extends from a proximal opening 412 thereof to a distal opening 432 thereof, and which is configured to receive passage of an elongate body of an implantable medical device therethrough, for example either of the bodies 10, 100 described above, in conjunction with FIGS. 1A-B and 2.

Figure 4B:
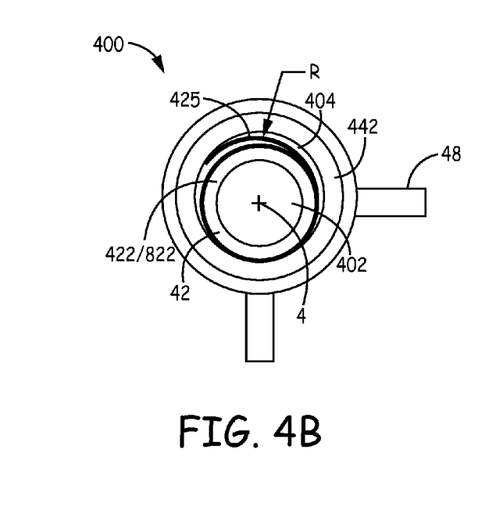
FIG. 4B is an end view of the tool of FIG. 4A in a pre- or post-deployment configuration, according to some embodiments.

FIG. 4A further illustrates deployment member 420 including an elastic cantilever element 425 secured to tubular sidewall 422 in proximity to a distal-most edge 42 (FIG. 4B) thereof that forms distal opening 432 of lumen 402. According to the illustrated embodiment, cantilever element 425 is spring biased to extend outward from sidewall 422, in a direction approximately orthogonal to a longitudinal axis 4 of tool 400, thus element 425 can facilitate engagement of a fixation element of the medical device body at an implant site, for example, helix fixation element 150 associated with body 100 or helix fixation element 15 associated with body 10 (FIGS. 1A-B), when the elongate body has been passed through lumen 402 and out through distal opening 432. But, when tool 400 is in a pre- or post-deployment configuration, for example, as illustrated in the end view of FIG. 4B, sheath lumen 404 receives deployment member sidewall 422 and cantilever element 425 therein, and sheath sidewall 442 pushes cantilever element 425 inward, toward longitudinal axis 4, against the spring bias thereof. FIG. 4B illustrates cantilever element 425 having a radius of curvature R that approximately conforms to a curvature of an outer surface of deployment member sidewall 422. With further reference to FIG. 4A, a distal-most edge 44 of sheath sidewall 442, which defines a distal opening 434 of sheath lumen 404, preferably extends in a plane that forms an acute angle α with longitudinal axis 4, so that edge 44 is tapered to facilitate the movement of cantilever element 425 proximally through distal opening 434 and into lumen 404, which compresses or pushes element 425 against the spring-biased thereof.

Figure 5:
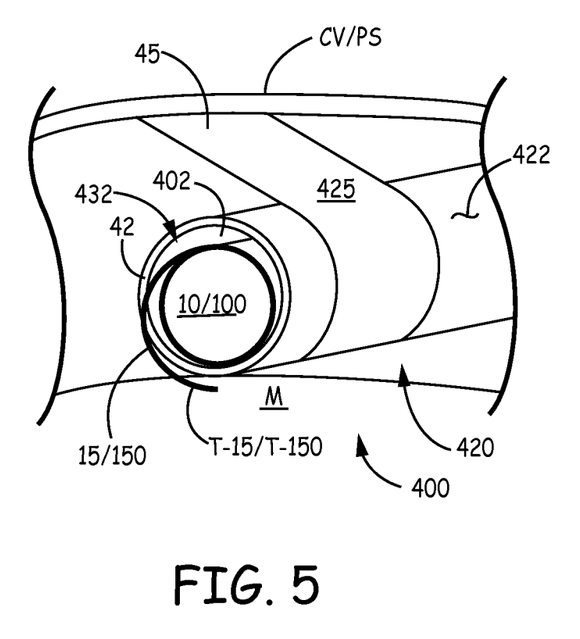
FIG. 5 is a perspective view cross-section schematic of a portion of a system for deployment of medical diagnostics and/or therapy at an implant site, according to some embodiments.

FIG. 5 is a perspective view cross-section schematic of a portion of the system that includes delivery tool 400 and either device body 10 or device body 100. FIG. 5 illustrates device body 10/100 having been loaded by an operator into deployment member lumen 402 of tool 400 for deployment, for example, within cardiac vein CV or between myocardium M and pericardial sac PS. FIG. 5 illustrates a free end 45 of elastic cantilever element 425 released from the constraint of sheath sidewall 442 and spring-biased outward to abut a wall generally opposite myocardium, either that of cardiac vein CV or pericardial sac PS. According to some embodiments, cantilever element 425 includes a radiopaque marker (not shown) being located in proximity to free end 45 to provide some fluoroscopic guidance to the operator for the orientation of deployment member 420. In some of these embodiments, deployment member sidewall 422 may include an additional radiopaque marker located opposite free end 45 and in proximity to distal opening 432 of deployment member lumen 402. FIG. 5 further illustrates the orientation cantilever element 425 causing distal opening 432 of lumen 402 to be offset toward myocardium M for the engagement of fixation element piercing tip T-15/T-150 therewith. With reference back to FIGS. 4A-B, a hub 428 of deployment member 420, which defines proximal opening 412 of lumen 402, includes a handle 48, and, according to some embodiments, handle 48 protrudes laterally from hub 428 in a direction that is approximately 90 degrees offset from the spring biased extension of cantilever element 425, about a circumference of sidewall 422 (FIG. 4B), for example, to provide the operator with an indication of the direction of the extension of element 425, either in addition to, or as an alternative to fluoroscopic visualization of the aforementioned radiopaque marker(s).

According to some exemplary embodiments, sheath 440 of tool 400 is constructed like a typical guiding catheter known in the art of interventional cardiology, and may have a diameter in the range of 6F (0.08 inch) to 14F (0.182 inch). Thus, sheath sidewall 442 may be formed by a braid-reinforced medical grade polymer, for example, one or more appropriate grades of polyether block amide (PEBAX®) reinforced with a stainless steel braid. Similarly, in the exemplary embodiments, deployment member sidewall 422 can be formed by any suitable medical grade polymer, such as one or more suitable grades of PEBAX®, and may also include some stainless steel braid reinforcement. In the exemplary context, sheath 440 and deployment member 420 should each have a sufficient length to reach an epicardial implant site from an appropriate venous access site, for example, subclavian or femoral. In some preferred embodiments, elastic cantilever element 425 is formed from a laser cut Nitinol tube, which is held in a fixture and heat treated, to set the outward spring-bias thereof, and then is secured to deployment member sidewall 422 in proximity to distal-most edge 42, for example, by reflow methods known in the art, or by insert molding, or by solvent or adhesive bonding. The aforementioned optional radiopaque marker may be a platinum iridium rivet like member embedded in free end 45 of cantilever element 425, or a relatively thin layer of gold, platinum or tungsten applied to free end 45 of cantilever element 425, and the additional optional radiopaque marker of deployment member sidewall 422 may be a gold or platinum insert secured in proximity to distal opening 432. Although not within the scope of the present invention, we contemplate the incorporation of an elastic cantilever element, similar to element 425, into the construction of an elongate body of a medical device.

Figure 6A:
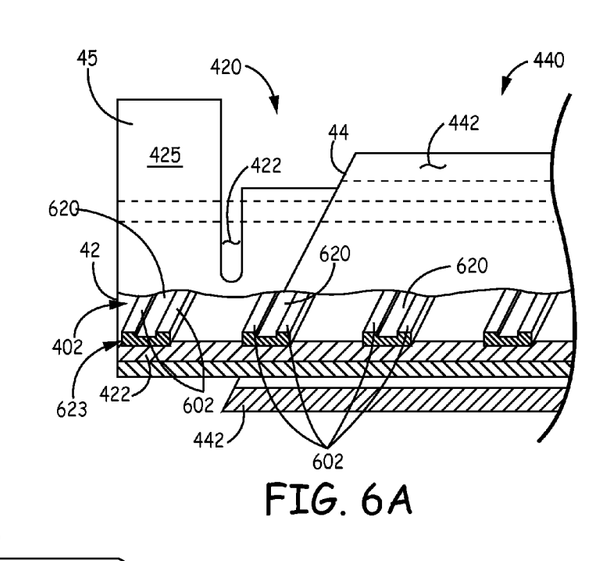
FIG. 6A is a plan view, with a partial cross-section, of a portion of the delivery tool, according to some embodiments.
Figure 6B:
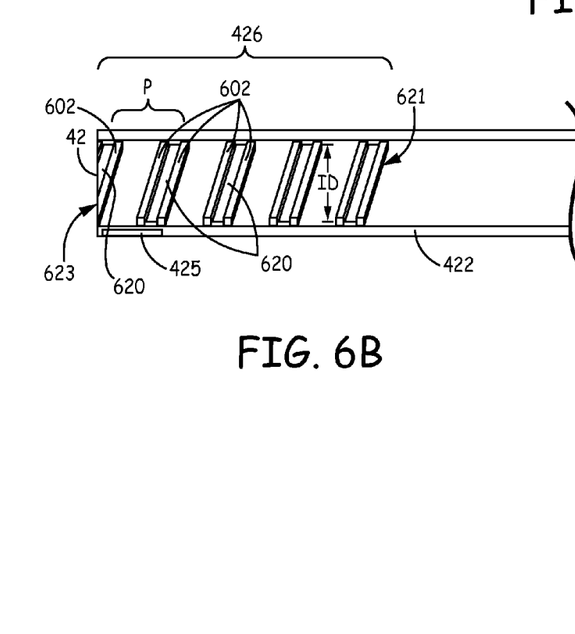
FIGS. 6B-C are longitudinal cross-sections of the portion of the tool shown in FIG. 6A, according to alternate embodiments.
Figure 6C:
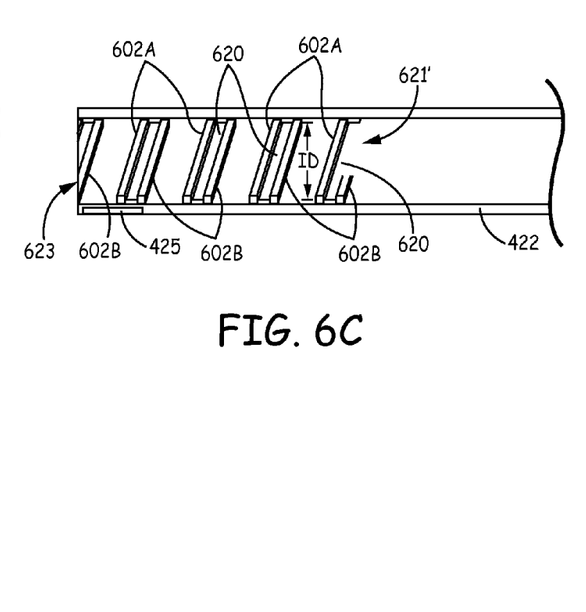

FIG. 6A is a plan view, with a partial cross-section, of a portion of the delivery tool 400, according to some embodiments that include a helical track 620; and FIGS. 6B-C are longitudinal cross-sections that shown alternate embodiments of track 620. FIGS. 6A-C illustrate helical track 620 extending around a perimeter of deployment member lumen 402 within a distal segment 426 of deployment member sidewall 422, which is terminated by distal-most edge 42 of sidewall 422. FIGS. 6A-C show a distal terminal end 623 of track 620 located in close proximity to distal-most edge 42 and generally opposite free end 45 of elastic cantilever element 425, when element 425 extends, according to the spring bias thereof, outward from sidewall 422. According to the illustrated embodiments, helical track 620 is configured receive passage of a helix fixation element of a medical device body therein (e.g., helix fixation element 15/150 of body 10/100), and thereby guide the piercing tip thereof (e.g., tip T-15/T-150) into engagement with tissue that is generally opposite free end 45 of extended cantilever element 425, for example, as illustrated in FIG. 5. FIGS. 6A-C further illustrate track 620 being formed by a pair of helically extending side rails 602 that protrude inward from an inner surface of sidewall 422. Track 620 and side rails 602 are preferably formed from a relatively hard medical grade plastic such as nylon, which may be coupled to the inner surface of sidewall 422. According to some preferred embodiments, track 620 and side rails 602 are initially formed as a molded component over which a portion of sidewall 422 is over-molded to form a subassembly that is attached to a remainder of sidewall 422, for example by solvent, heat or adhesive bonding methods known in the art. This subassembly may further include cantilever element 425 insert molded together therewith during the over-molding process. Alternately, track 620 may be defined by a groove integrally formed into the inner surface of sidewall 422 along distal segment 426 thereof. A relatively hard surface of track 620 may be preferred to prevent binding of helix fixation element 15/150 therein.

According to some embodiments, for example, illustrated in FIG. 6B, each side rail 602 extends around a same number of turns to form an entirety of track 620, from a proximal terminal end 621 thereof to distal terminal end 623. According to some alternate embodiments shown in FIG. 6C, a first of the pair of side rails 602, designated 602A, extends around a first number of turns, and a second of the pair of side rails 602, designated 602B, extends around a second number of turns that is fewer than the first, so that a proximal terminal end 621' of track 620 is formed by only first side rail 602A for between approximately one fourth turn to one turn (i.e., 90-360 degrees). This open proximal terminal end 621' of track 620 may help to guide helix fixation element 15/150 into engagement with track, when an operator loads device body 10/100 into deployment member lumen 402 from proximal opening 412 (FIG. 4A). In either case, a pitch P and an inner diameter ID of helical track 620 approximately match a pitch and maximum outer diameter of helix fixation element 15/150. According to some system embodiments, an elongate body of a medical device includes an enlarged stop formed in a junction between the helix fixation member and the body so that track 620 will need to accommodate the stop as well.

Figure 7:
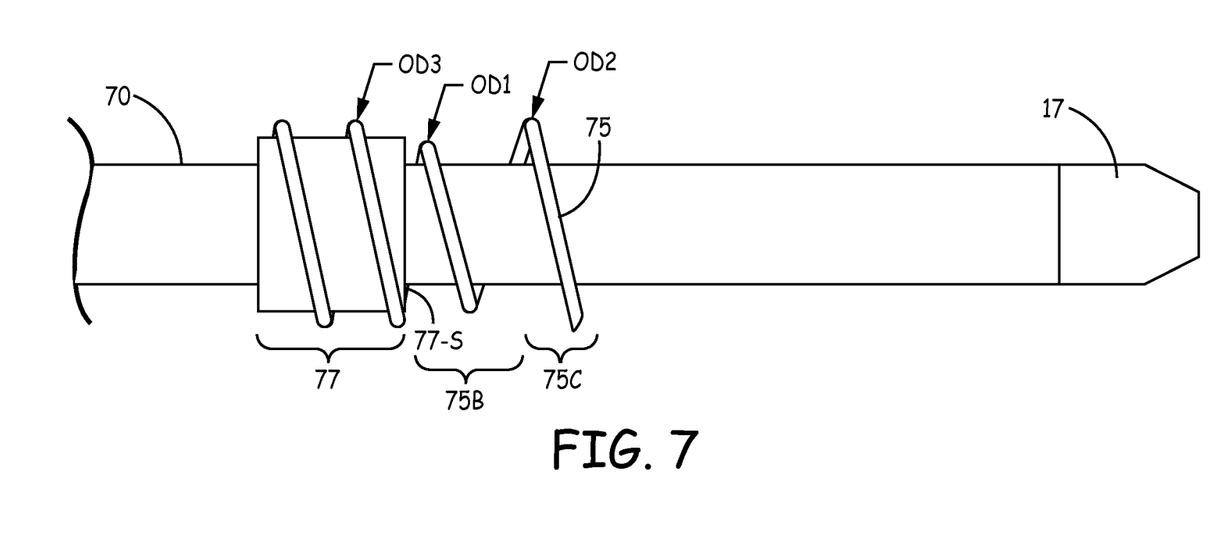
FIG. 7 is a plan view of a portion of another exemplary implantable medical device.

FIG. 7 is a plan view of a portion of another exemplary implantable medical device, which includes a stop 77-S formed by a junction 77 between a helix fixation member 75 and an elongate body 70 of the device, according to some system embodiments. FIG. 7 illustrates helix fixation element 75 including a first segment, which is embedded within junction 77, a second segment 75B, which has a first outer diameter OD1, and a third segment 75C, which has a second outer diameter OD2 and is terminated by a distal piercing tip T-75. FIG. 7 further illustrates junction 77 being formed with a helical profile that matches a pitch of helix fixation element 75 and has an outer diameter OD3, wherein second outer diameter OD2 of helix fixation element 75 is greater than or equal to outer diameter OD3. Thus, with reference back to FIGS. 6B-C, according to system embodiments that include deployment member 420 (or a deployment member 820, described below) and the device of FIG. 7, pitch P of helical track 620 matches that of helix fixation member 75 and junction 77, and inner diameter ID of helical track 620 is approximately equal second outer diameter OD2 of helix fixation member, so that track 620 may accommodate passage therethrough of stop 77-S formed by junction 77.

Figure 8A:
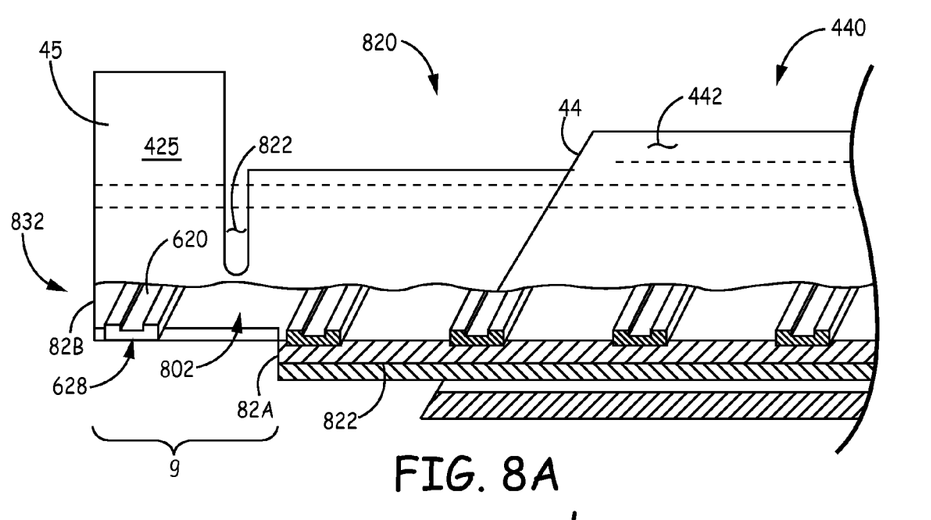
FIG. 8A is a plan view, with a partial cross-section, of a portion of a delivery tool, according to another embodiment.
Figure 8B:
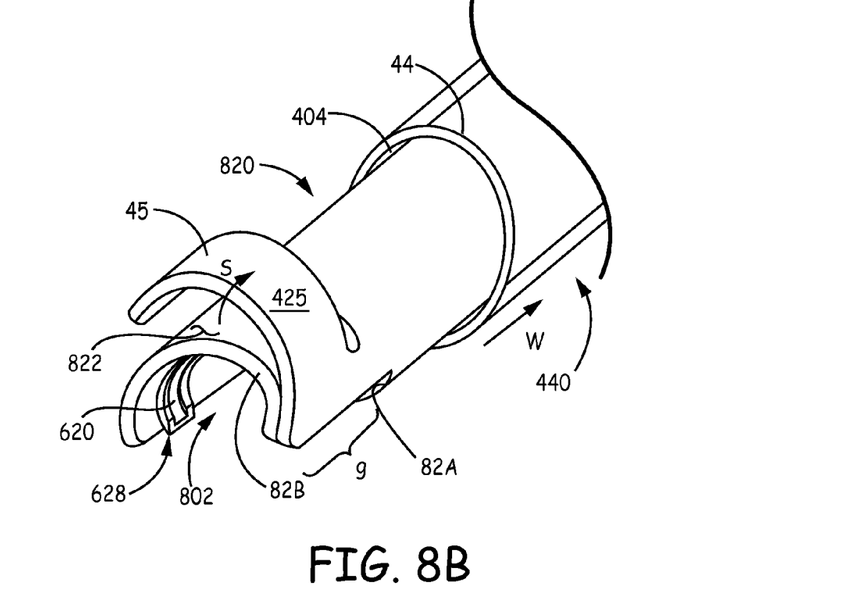
FIG. 8B is a perspective view of the portion of the tool of FIG. 8A.
Figure 8C:
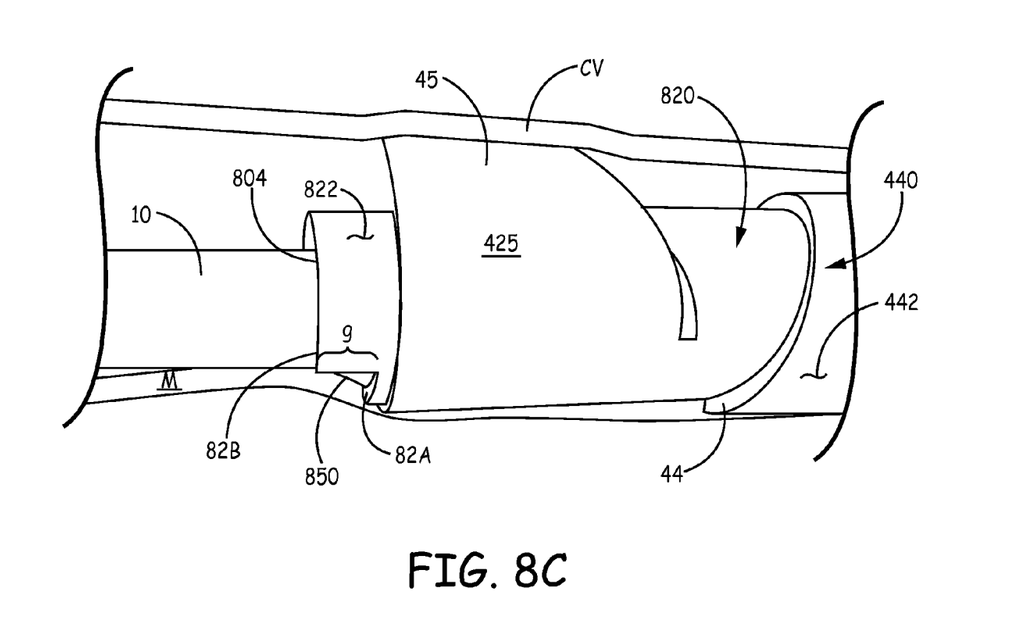
FIG. 8C is a perspective view cross-section schematic of another system that includes the tool of FIG. 8A-B, according to some embodiments.

Turning now to FIGS. 8A-C an alternate embodiment of a delivery tool will be described. FIG. 8A is a plan view, with a partial cross-section, of a portion of the delivery tool, which includes the above-described sheath 440 receiving passage of deployment member 820 therein. FIG. 8A illustrates deployment member 820 including a tubular sidewall 822, which, like sidewall 422 of deployment member 420, forms an elongate lumen 802 extending from a proximal opening thereof (not shown) to a distal opening 832 thereof, wherein lumen 802 is configured to receive passage of an elongate body of an implantable medical device therethrough, for example either of the bodies 10, 100 described above, in conjunction with FIGS. 1A-B and 2. Deployment member 820 is also shown including elastic cantilever element 425 secured to sidewall 822 in proximity to distal opening 832. In contrast to deployment member 420, a distal most edge of sidewall 822 of deployment member 820, which defines distal opening 832, includes a first section 82A and a second section 82B, wherein first section 82A is recessed from second section 82B such that a longitudinal gap g exists between first and second sections 82A, 82B. FIGS. 8A-B further illustrate deployment member 820 including helical track 620, which may be configured according to any of the embodiments described above, but which has a distal terminal end 628 lying within longitudinal gap g. According to the illustrated embodiment, gap g may be approximately one half the pitch length of helical track 620; and, with reference to FIGS. 8B-C, sections 82A, 82B and gap g form a kind of window being located opposite free end 45 of elastic cantilever element 425, when cantilever element 425 extends outward, per arrow S, having been released from constraint within lumen 404 of sheath 440, for example, when the operator withdraws sheath 440, per arrow W, relative to deployment member 820.

FIG. 8C is a perspective view cross-section schematic of a system that includes the tool of FIG. 8A-B, wherein elongate medical device body 10 has been advanced distally into cardiac vein CV, through deployment member lumen 802, and sheath 440 has been withdrawn relative to deployment member 820 and body 10 so that free end 45 of elastic cantilever element 425 abuts the wall of cardiac vein CV that is opposite myocardium M. According to some methods, an operator may position sheath 440 within a body of a patient, so that distal-most edge 44 of sidewall 442 is located in cardiac vein CV, prior to advancing deployment member 820 (alternately deployment member 420) and medical device body 10 (alternately device body 100) through sheath 440 and into cardiac vein CV. In some cases, device body 10/100 is advanced through the positioned sheath 440 together with deployment member 820/420, having been preloaded into deployment member 820/420 so that helix fixation member 15/150 is engaged in helical track 620 with piercing tip T-15/T-150 located in proximity to distal terminal end 628 of track 620 (alternately distal terminal end 623 in deployment member 420). FIG. 8C illustrates cantilever element 425 forcing the above-described window, formed by sections 82A, 82B and gap g, into contact with myocardium M to create a piercing site 850. Although not shown in FIG. 8C, it may be appreciated, with reference to FIGS. 1B and 8B, that piercing tip T-15 of helix fixation member 15, having been guided by passage through helical track 620, is oriented to engage with tissue at piercing site 850. Thus, the operator can rotate body 10 to initially engage helix fixation member 15 with myocardium M at site 850, and then continue to rotate body 10 to fully engage member 15 for implant, and then retract deployment member 820 into sheath 440, relative to the implanted body 10, so that elastic cantilever element 425 is contained within sheath lumen 404, for example, as shown in FIG. 4B, prior to withdrawing the delivery tool from over the implanted device body 10. According to some preferred embodiments, cantilever element 425 is C-shaped, not extending around an entire perimeter of sidewall 422 to allow for withdrawal methods that employ slitting through sidewall 422.

In the foregoing detailed description, the invention has been described with reference to specific embodiments. However, it may be appreciated that various modifications and changes can be made without departing from the scope of the invention as set forth in the appended claims.

The invention claimed is:

1. A delivery tool for an implantable medical device, the tool comprising:
    a deployment member comprising a tubular sidewall and an elastic cantilever element, the tubular sidewall defining an elongate lumen of the deployment member that extends along a longitudinal axis of the tool, from a proximal opening of the lumen to a distal opening of the lumen, the lumen being configured to receive passage of an elongate body of the medical device therethrough, and the elastic cantilever element being secured to the tubular sidewall in proximity to the distal opening of the lumen, the cantilever element being spring biased to extend outward from the sidewall, in a direction approximately orthogonal to the longitudinal axis, and being formed to bend inward around the longitudinal axis of the tool, from where the element is secured to the tubular sidewall; and
    a sheath including a tubular sidewall, the sheath sidewall defining an elongate lumen of the sheath that extends along the longitudinal axis of the tool, from a proximal opening of the sheath lumen to a distal opening of the sheath lumen, the sheath lumen being configured to receive passage of both the tubular sidewall of the deployment member and the elastic cantilever element of the deployment member therethrough, the cantilever element, when received within the sheath lumen, being pushed inward by the sheath sidewall, against the spring bias thereof, to bend around the tool axis; and
    wherein the elastic cantilever element of the deployment member, when bending around the longitudinal axis of the tool, has a radius of curvature that approximately conforms to a curvature of an outer surface of the tubular sidewall of the deployment member.

2. The tool of claim 1, wherein the sheath sidewall has a distal-most edge that defines the distal opening of the sheath lumen, the distal-most edge extending in a plane that forms an acute angle with respect to the longitudinal axis of the tool.

3. The tool of claim 1, wherein:
    the deployment member sidewall has a distal-most edge that defines the distal opening of the deployment member lumen;
    the deployment member further comprises a helical track extending around a perimeter of the deployment member lumen, within a distal segment of the deployment member sidewall, the distal segment being terminated by the distal-most edge; and
    the helical track has a distal terminal end located in close proximity to the distal-most edge of the deployment member sidewall, the location of the distal terminal end of the track being generally opposite a free end of the cantilever element, when the cantilever element extends outward from the deployment member sidewall according the spring bias thereof.

4. The tool of claim 3, wherein the deployment member includes a pair of helically extending side rails spaced longitudinally apart from one another to form the helical track along the distal segment of the deployment member sidewall, the side rails protruding inward from an inner surface of the deployment member sidewall, toward the longitudinal axis of the tool.

5. The tool of claim 4, wherein a first side rail of the pair of side rails extends around a first number of turns, and a second side rail of the pair of side rails extends around a second number turns, the second number of turns being less that the first number of turns such that a proximal terminal end of the helical track is formed by only the first side rail for between approximately one fourth of a turn and one turn.

6. The tool of claim 4, wherein the pair of side rails comprise a molded component, the distal segment of the deployment member sidewall being over-molded onto the molded component to form a subassembly, and the subassembly being attached to a remainder of the deployment member sidewall.

7. The tool of claim 6, wherein the subassembly further comprises the cantilever element insert molded together with the distal segment of the sidewall.

8. The tool of claim 3, wherein:
    the distal-most edge of the deployment member sidewall includes a first section and a second section, the first section being recessed from the second section along the longitudinal axis of the tool such that a longitudinal gap between the first section and the second section is approximately one half a pitch length of the helical track;

the elastic cantilever element is secured to the deployment member sidewall between the first and second sections of the distal-most edge of the sidewall; and the location of the distal terminal end of the helical track lies within the gap.

9. The tool of claim 1, wherein the deployment member further includes a hub defining the proximal opening of the lumen thereof, the hub including a handle that protrudes laterally therefrom in a direction that is approximately 90 degrees offset from the spring biased extension of the elastic cantilever element, about a circumference of the deployment member sidewall.

10. A system for deploying medical diagnostics and/or therapy, the system comprising an implantable medical device including an elongate body for delivery of the therapy therethrough and a helix fixation element coupled to the body, and a delivery tool for implanting the elongate body, the delivery tool comprising:

a deployment member comprising a tubular sidewall and an elastic cantilever element, the tubular sidewall defining an elongate lumen of the deployment member that extends along a longitudinal axis of the tool, from a proximal opening of the lumen to a distal opening of the lumen, the lumen being configured to receive passage of the elongate body therethrough, and the elastic cantilever element being secured to the tubular sidewall in proximity to the distal opening of the lumen, the cantilever element being spring biased to extend outward from the sidewall, in a direction approximately orthogonal to the longitudinal axis, and being formed to bend inward around the longitudinal axis of the tool, from where the element is secured to the tubular sidewall; and a sheath including a tubular sidewall, the sheath sidewall defining an elongate lumen of the sheath that extends along the longitudinal axis of the tool, from a proximal opening of the sheath lumen to a distal opening of the sheath lumen, the sheath lumen being configured to receive passage of both the tubular sidewall of the deployment member and the elastic cantilever element of the deployment member therethrough, the cantilever element, when received within the sheath lumen, being pushed inward by the sheath sidewall, against the spring bias thereof, to bend around the tool axis; and wherein the elastic cantilever element of the deployment member, when bending around the longitudinal axis of the tool, has a radius of curvature that approximately conforms to a curvature of an outer surface of the tubular sidewall of the deployment member.

11. The system of claim 10, wherein the tubular sidewall of the delivery tool sheath has a distal-most edge that defines the distal opening of the sheath lumen, the distal-most edge extending in a plane that forms an acute angle with respect to the longitudinal axis of the tool.

12. The system of claim 10, wherein:

the tubular sidewall of the delivery tool deployment member has a distal-most edge that defines the distal opening of the deployment member lumen;

the delivery tool deployment member further comprises a helical track extending around a perimeter of the deployment member lumen, within a distal segment of the deployment member sidewall, the distal segment being terminated by the distal-most edge, and the helical track being configured to receive passage of the helix fixation element therein; and the helical track includes a distal terminal end located in close proximity to the distal-most edge of the delivery tool deployment member sidewall, the location of the distal terminal end being generally opposite a free end of the elastic cantilever element of the delivery tool deployment member, when the cantilever element extends outward from the deployment member sidewall according the spring bias thereof.

13. The system of claim 12, wherein the delivery tool deployment member includes a pair of helically extending side rails spaced longitudinally apart from one another to form the helical track along the distal segment of the deployment member sidewall, the side rails protruding inward from an inner surface of the deployment member sidewall, toward the longitudinal axis of the tool.

14. The system of claim 13, wherein a first side rail of the pair of side rails extends around a first number of turns, and a second side rail of the pair of side rails extends around a second number turns, the second number of turns being less that the first number of turns such that a proximal terminal end of the helical track is formed by only the first side rail for between approximately one fourth of a turn and one turn.

15. The system of claim 13, wherein the pair of side rails of the delivery tool deployment member comprise a molded component, the distal segment of the deployment member sidewall being over-molded onto the molded component to form a subassembly, and the subassembly being attached to a remainder of the deployment member sidewall.

16. The system of claim 15, wherein the subassembly further comprises the cantilever element of the delivery tool deployment member insert molded together with the distal segment of the sidewall.

17. The system of claim 12, wherein:

the implantable elongate body includes a junction at which the helix fixation element is coupled, being embedded therein, the junction being formed with a helical profile;

the helix fixation element includes first, second, and third segments, the first segment being embedded within the junction, the second segment extending from the first segment to the third segment, the third segment being terminated by a distal-most piercing tip of the helix fixation element, and the helical profile of the junction matching a pitch of the second and third segments of the helix fixation element, and having an outer diameter greater than that of the second segment;

the third segment of the helix fixation element has an outer diameter greater than that of the second segment of the helix fixation element, and greater than or equal to that of the junction; and the helical track of the delivery tool deployment member has an inner diameter approximately equal to the outer diameter of the third segment of the helix fixation element.

18. The system of claim 12, wherein:

the distal-most edge of the tubular sidewall of the delivery tool deployment member includes a first section and a second section, the first section being recessed from the second section along the longitudinal axis of the tool such that a longitudinal gap between the first section and the second section is approximately one half a pitch length of the deployment member helical track;

the elastic cantilever element is secured to the deployment member sidewall between the first and second sections of the distal-most edge of the sidewall; and the location of the distal terminal end of the deployment member helical track lies within the gap.

19. The system of claim 10, wherein the delivery tool deployment member further includes a hub defining the proximal opening of the lumen thereof, the hub including a handle that protrudes laterally therefrom in a direction that is approximately 90 degrees offset from the spring biased extension of the elastic cantilever element of the delivery tool deployment member, about a circumference of the deployment member sidewall.

\* \* \* \* \*